(12) United States Patent
Bredno et al.

(10) Patent No.: US 9,125,616 B2
(45) Date of Patent: Sep. 8, 2015

(54) COLLATERAL BLOOD FLOW ASSESSMENT

(75) Inventors: Joerg Bredno, San Francisco, CA (US); Max Wintermark, Charlottesville, VA (US)

(73) Assignee: Koninklijke Philips N.V., Eindhoven (NL)

( * ) Notice: Subject to any disclaimer, the term of this patent is extended or adjusted under 35 U.S.C. 154(b) by 563 days.

(21) Appl. No.: 13/509,804

(22) PCT Filed: Nov. 18, 2010

(86) PCT No.: PCT/IB2010/055265
§ 371 (c)(1),
(2), (4) Date: May 15, 2012

(87) PCT Pub. No.: WO2011/070467
PCT Pub. Date: Jun. 16, 2011

(65) Prior Publication Data
US 2012/0238888 A1    Sep. 20, 2012

Related U.S. Application Data

(60) Provisional application No. 61/285,207, filed on Dec. 10, 2009.

(51) Int. Cl.
*A61B 5/02* (2006.01)
*A61B 6/00* (2006.01)
*A61B 8/06* (2006.01)
*G01R 33/563* (2006.01)

(52) U.S. Cl.
CPC .............. *A61B 6/481* (2013.01); *A61B 5/02028* (2013.01); *A61B 6/507* (2013.01); *A61B 8/06* (2013.01); *G01R 33/56366* (2013.01)

(58) Field of Classification Search
CPC .... A61B 5/026; A61B 5/0261; A61B 5/0263; A61B 5/0265; A61B 8/08; A61B 6/504; A61B 6/507
USPC ........................................................ 600/504
See application file for complete search history.

(56) References Cited

U.S. PATENT DOCUMENTS

2002/0161292 A1* 10/2002 Wintermark et al. ......... 600/407
2003/0073913 A1*  4/2003 Gingrich et al. ............. 600/504
2011/0028850 A1*  2/2011 Schuhrke et al. ............ 600/476

OTHER PUBLICATIONS

Taylor et al. Image-Based Modeling of Blood Flow and Vessel Wall Dynamics: Applications, Methods and Future Directions. Annals of Biomedical Engineering, vol. 38, No. 3, Mar. 2010: pp. 1188-1203.*
Taylor et al. Patient Specific Modeling of Cardiovascular Mechanics. Annu. Rev. Biomed. eng. 2009, 11:109-34.*
Waechter et al. Using flow information to support 3D vessel reconstruction from rotational angiography. Medical Physics 35, 3302 (2008).*
Camargo, E. C., et al.; Neuroimaging of Ischemia and Infarction; 2005; The American Society for Experimental NeuroTherapeutics, Inc.; vol. 2; pp. 265-276.

(Continued)

*Primary Examiner* — Etsub Berhanu

(57) ABSTRACT

A method includes obtaining both first inflow and first perfusion metrics for non-healthy tissue of interest, obtaining both second inflow and second perfusion metrics for healthy tissue of interest, and concurrently presenting both the first flow and perfusion metrics for the non-healthy tissue of interest and both the second flow and perfusion metrics for the healthy tissue of interest.

17 Claims, 2 Drawing Sheets

(56) References Cited

OTHER PUBLICATIONS

Berry, C., et al.; Importance of Collateral Circulation in Coronary Heart Disease; 2007; European Heart Journal; vol. 28; pp. 278-291.

Matsuo, H., et al.; Validation of Collateral Fractional Flow Reserve by Myocardial Perfusion Imaging; 2002; Circulation; vol. 105; pp. 1060-1065.

Murata, K., et al.; The influence of coronary collateral flow on the assessment of myocardial perfusion by videodensitometry; 1997; Cardiovascular Research; 33(2)abstract.

Soares, B. P., et al.; Reperfusion is a More Accurate Predictor of Follow-up Infarct Volume Than Recanalization; 2009; Stroke; A Journal of Cerebral Circulation; 41(1)E34-E40.

Tan, J. C., et al.; Systematic Comparison of Perfusion-CT and CT-Angiography in Acute Stroke Patients; 2007; Annals of Neurology; 61(6)533-543.

Vogel, R., et al.; Collateral-flow measurements in humans by myocardial contrast echocardiography: validation of coronary pressure-derived collateral-flow assessment; 2005; European Heart Journal Advance Access; doi:10.1093/eurheartj/ehi585.

* cited by examiner

COLLATERAL BLOOD FLOW ASSESSMENT

CROSS REFERENCE TO RELATED APPLICATIONS

This application claims the benefit of U.S. provisional application Ser No. 61/285,207 filed Dec. 10, 2009, which is incorporated herein by reference.

The following generally relates to assessing collateral blood flow in tissue of interest based on imaging data from one or more imaging modalities such as computed tomography (CT), magnetic resonance (MR), positron emission tomography (PET), single photon emission computed tomography (SPECT), x-ray radiography (X-Ray), ultrasound (US), and/or other imaging modalities.

Quantitative or semi-quantitative measurements of arterial blood flow and tissue perfusion provide information that can be used for stroke prevention, diagnosis, therapy decision, and outcome control. Collateral blood flow, which is blood flow through smaller arterial pathways that connect neighboring regions primarily supplied by different major arteries, has been identified as information that can be used to predict acute stroke outcome and to assess risk for patients with carotid stenosis.

While potentially beneficial for risk indication of carotid stenosis and a predictor of acute stroke outcome, the smaller collateral pathways have not been and generally are not well-suited to be imaged for such applications. Rather, static angiogram images, which provide measurements of intra-arterial lumen, arterial blood flow or velocity measurements, and tissue perfusion images are visually assessed and analyzed sequentially. Unfortunately, information on the amount of collateral inflow to perfuse tissue in an affected territory is not presently available from imaging data.

Conventionally, a static rating for collateral flow can be determined in perfusion territories with a completely occluded major feeding artery. For these cases, the amount of contrast agent visible in vessels behind a complete occlusion provides information on collateral inflow into this territory. More particularly, a presence of contrast agent downstream from a complete occlusion indicates collateral flow, and an absence of contrast agent downstream from a complete occlusion indicates lack of collateral flow.

Aspects of the present application address the above-referenced matters and others.

According to one aspect, a method includes obtaining both first inflow and first perfusion metrics for non-healthy tissue of interest, obtaining both second inflow and second perfusion metrics for healthy tissue of interest, and concurrently presenting both the first flow and perfusion metrics for the non-healthy tissue of interest and both the second flow and perfusion metrics for the healthy tissue of interest.

In another embodiment, a method includes obtaining both first inflow and first perfusion metrics for the non-healthy tissue of interest and both second inflow and second perfusion metrics for healthy contralateral tissue of interest, computing a relative inflow metric based on the inflow metrics of the non-healthy and the healthy contralateral tissue of interest and a relative perfusion metric based on the perfusion metrics of the non-healthy and the healthy contralateral tissue of interest, and generating a signal indicative of a collateral grading score based on the relative inflow and perfusion metrics.

In another embodiment, a system includes an imaging data supplementor that supplements imaging data of non-healthy tissue of interest and healthy tissue of interest with inflow and perfusion metrics for the non-healthy tissue of interest and the healthy tissue of interest.

The invention may take form in various components and arrangements of components, and in various steps and arrangements of steps. The drawings are only for purposes of illustrating the preferred embodiments and are not to be construed as limiting the invention.

The following generally relates to assessing collateral blood flow (which is blood flow in smaller vessels that can support a main vessel such as an artery in supplying blood to tissue) based on imaging data. As described in greater detail below, in one instance this includes presenting both an inflow (into a feeding artery) metric and a local tissue perfusion metric for both non-healthy tissue (e.g., diseased tissue or at risk tissue) and healthy contralateral tissue (i.e., healthy tissue of the same type) with or without the imaging data, and/or generating a collateral grading score based thereon indicative of the collateral blood flow. The metrics and/or score can be used in connection with assessing an acute ischemic event and/or risk of such an event in the future.

For sake of brevity and explanatory purposes, the following is described in the context of brain tissue. Generally, the brain consists of left and right hemispheres, and inflow in both hemispheres is substantially similar and perfusion in both hemispheres is substantially similar. Hence, inflow and perfusion in a healthy hemisphere can be used as a reference for inflow and perfusion in a non-healthy (e.g., diseased tissue or at risk tissue) hemisphere, such as a hemisphere affected by stroke. As such, for the below discussion, non-healthy tissue generally refers to a hemisphere or a certain region in a hemisphere of the brain affected by stroke and healthy contralateral tissue generally refers to the other (non-affected) hemisphere or the corresponding region of the brain. Preferably, such a region is a perfusion territory that receives its main blood supply from one distinct artery.

However, it is to be appreciated that the following is not limited to brain tissue or tissue affected by stroke. For example, inflow and perfusion of the healthy hemisphere of the brain can be replaced or supplemented with inflow and perfusion of healthy non-brain tissue with inflow and perfusion characteristics similar to that of the inflow and perfusion characteristics of the brain. In addition, collateral blood flow for other (non-brain) non-healthy tissue can be similarly assessed based on brain tissue or other tissue with inflow and perfusion characteristics similar to the inflow and perfusion characteristics of the tissue under study (the tissue of interest).

Figure 1:
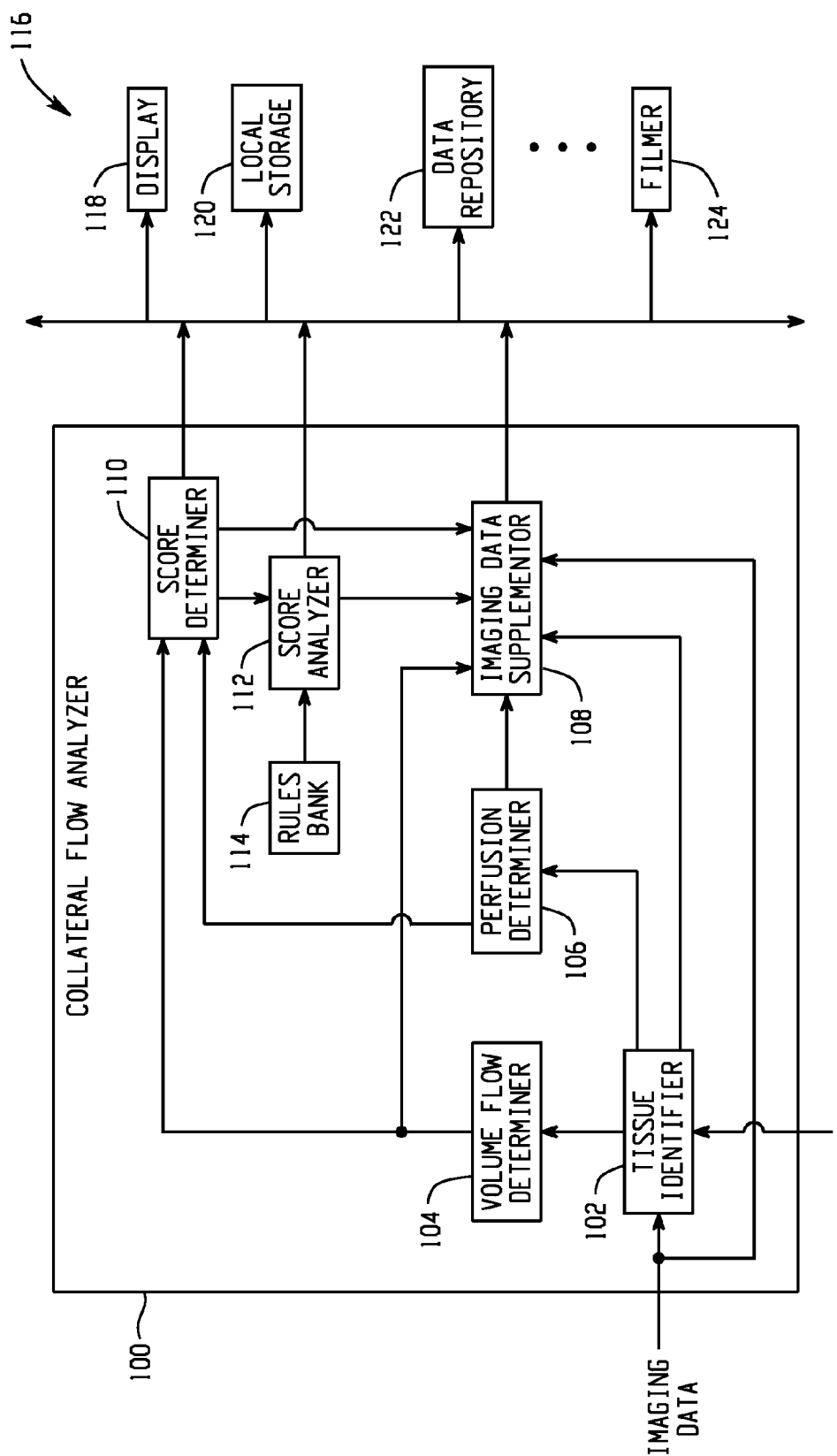
FIG. 1 illustrates an example collateral flow analyzer that analyzes collateral flow of non-healthy (diseased or at-risk) tissue based on inflow and perfusion metrics of both the non-healthy tissue and healthy contralateral tissue and/or a collateral grading score based thereon.

FIG. 1 illustrates an example collateral flow analyzer 100.

As shown, the collateral flow analyzer 100 can obtain and/or receive imaging data from various imaging modalities such as computed tomography (CT), magnetic resonance (MR), positron emission tomography (PET), single photon emission computed tomography (SPECT), x-ray radiography (X-Ray), ultrasound (US), and/or other imaging modalities.

Examples of suitable imaging data include, but are not limited to, one or more of contrast-enhanced CT data, CTA data, contrast-enhanced MRI data, MRA data, SPECT data, PET data, Doppler Ultrasound data, interventional X-ray data, and/or other imaging data.

A tissue identifier 102 identifies tissue of interest in the imaging data. The illustrated tissue identifier 102 identifies such tissue based on a signal representing a predetermined tissue type selected via user input, a default parameter, a selected imaging protocol, etc. By way of example, in one instance the predetermined tissue type is brain tissue, for example, of a stroke patient undergoing a stroke study. In this instance, the predetermined tissue may include both stroke affected brain hemisphere (disease tissue or at-risk tissue) and the healthy (non stroke affected) brain hemisphere.

The tissue identifier 102 can employ various algorithms for identifying the tissue of interest in the imaging data. Suitable examples include, but are not limited to, automatic segmentation, semi-automatic segmentation, manual (user interactive) segmentation, model based registration (e.g., registration to atlas data), images fused with anatomical image data of the same field of view, and/or other segmentation techniques. The geometry of arteries and/or other anatomical structure and their respective perfusion territories can be determined from CTA data, MRA data, and/or other data that includes similar information.

A volume flow determiner 104 determines arterial blood volume inflow (Q) (and/or velocity (v)) for the identified tissue, including for both the healthy and the non-healthy (affected or at-risk) brain hemispheres. Such information can be determined from Doppler ultrasound, phase-contrast MR, other MR, interventional X-ray (e.g., blood flow estimates from arterial contrast agent concentration), and/or other imaging data. In another embodiment, the volume flow determiner 104 is omitted, and the blood inflow information is determined by and/or obtained from an apparatus or memory remote from the collateral flow determiner 104.

A perfusion determiner 106 determines local tissue perfusion (P), such a cerebral blood flow (CBF), for the identified tissue, including both the healthy and the non-healthy (affected or at-risk) brain hemispheres. The local tissue perfusion can be determined from dynamic, contrast-enhanced CT, dynamic, contrast-enhanced MRI, non-contrast-enhanced MRI, SPECT, PET, and/or other imaging data. An average local perfusion for the healthy and non-healthy tissue can be determined as a mean or median value from the corresponding segmented imaging data. Likewise, in another embodiment, the perfusion determiner 106 is omitted, and local tissue perfusion information is determined by and/or obtained from an apparatus or memory remote from the collateral flow determiner 104.

An imaging data supplementor 108 supplements the segmented imaging data from the tissue identifier 102 and/or the imaging data with the inflow and perfusion information. In one instance, this includes generating a color map or the like with different colors corresponding to different flow and perfusion values, and the color map is overlaid or superimposed over the segmented image data and/or image data. Additionally or alternatively, a numerical value corresponding to the flow and perfusion map is overlaid or superimposed over the segmented image data and/or image data. Additionally or alternatively, other approaches for supplementing imaging data are also contemplated herein.

A score determiner 110 determines a collateral grading score, or a signal indicative thereof, based on the inflow and perfusion information. For the collateral grading score, the score determiner 110 computes a relative inflow metric $$\frac{Q_{contra} - Q}{Q_{contra}},$$

which indicates a reduction in inflow in the non-healthy tissue relative to the healthy tissue, and a relative perfusion metric $$\frac{p_{contra} - p}{p_{contra}},$$

which indicates a reduction in perfusion in the non-healthy tissue relative to the healthy tissue.

From these metrics, the score determiner 110 determines a collateral grading score C based on EQUATION 1:

$$C = \frac{Q_{contra} - Q}{Q_{contra}} - \frac{p_{contra} - p}{p_{contra}}, \qquad \text{EQUATION 1}$$

which compares the reduction of arterial inflow in the non-healthy tissue to the reduction of tissue perfusion (if any) in the non-healthy tissue based on the inflow in the healthy tissue and the perfusion in the healthy tissue.

With Equation 1, C=0 where the reduction in perfusion in the non-healthy tissue is proportional to the reduction in inflow in the non-healthy tissue. This indicates no or substantially no collateral flow. Where perfusion in the healthy and non-healthy tissue is the same, a score C in the range of $0 < C \le 1$ indicates a fraction of the inflow of the non-healthy tissue that is provided by collateral pathways.

A score analyzer 112 analyzes the score C based on a set of rules in a rules bank 114 and generates a signal indicative of the analysis. For example, a rule may indicate that where C=0 the score analyzer 112 generates a signal indicating that collateral flow is non-existent or substantially non-existent (as the reduction in inflow for the non-healthy tissue is followed by an equal reduction in perfusion for the non-healthy tissue). Another rule may indicate that where C=X (wherein $0 < X \le 1$) the score analyzer 112 generates a signal indicating that the fraction of the normal inflow provided by collateral flow is X % of the normal flow (as the reduction in inflow for the non-healthy tissue is greater than the reduction in perfusion for the non-healthy tissue). The rules bank 114 may additionally or alternatively include other rules.

The supplemented imaging data, the supplemented segmented imaging data, the inflow metrics, the perfusion metrics, the collateral grading score, the results of the analysis, and/or other information can be provided to one or more output devices 116, including, but not limited to, a display 118, local storage 120, a data repository 122 (e.g., a RIS and/or HIS), a filmer 124, and/or other output device.

The display 118 can present various information. In one instance, the segmented imaging data for the healthy and non-healthy tissue are concurrently presented respectively along with corresponding inflow and perfusion information such as color maps, numerical values, etc. Such a presentation allows a clinician to visually observe flow and perfusion information for the healthy and non-healthy tissue. This allows the clinician to compare inflow to both healthy and non-healthy tissue and perfusion of the healthy and non-healthy tissue.

This may allow the clinician to assess collateral flow of the non-healthy tissue. By way of example, where the inflow of the non-healthy tissue is less than the inflow of the healthy tissue and the perfusion for both tissues is the same or about the same, this information indicates that the collateral flow for the non-healthy tissue is compensating for the decrease inflow. The comparison, depending on the inflow and perfusion data, may indicate other information.

In view of the foregoing, a clinician can assess collateral flow of the non-healthy tissue, for example, where there is a reduction in inflow between the healthy tissue and non-healthy tissue but either no reduction in perfusion or a reduction in perfusion in the non-healthy tissue that is less than the reduction in inflow in the healthy tissue and/or for other situations. Additionally or alternatively, the score C is presented via the display 118, providing similar information regarding the collateral flow. The score provides the clinician with a value indicative of the collateral flow. Additionally or alternatively, the result of the analysis is presented via the display 118, providing similar information regarding the collateral flow.

It is to be appreciated that the illustrated collateral flow analyzer 100 can be part of a computing system that includes one or more processors that execute computer readable instructions encoded in computer readable storage medium thereof.

Figure 2:
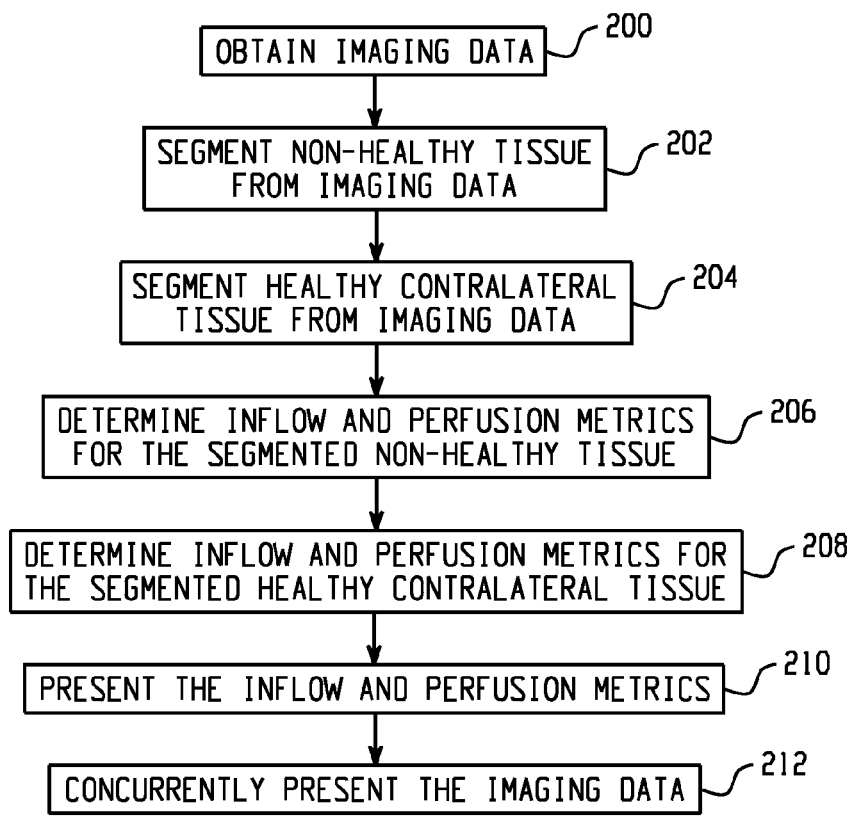
FIG. 2 illustrates an example method for assessing collateral flow based on inflow and perfusion metrics for both non-healthy tissue and healthy contralateral tissue.
Figure 3:
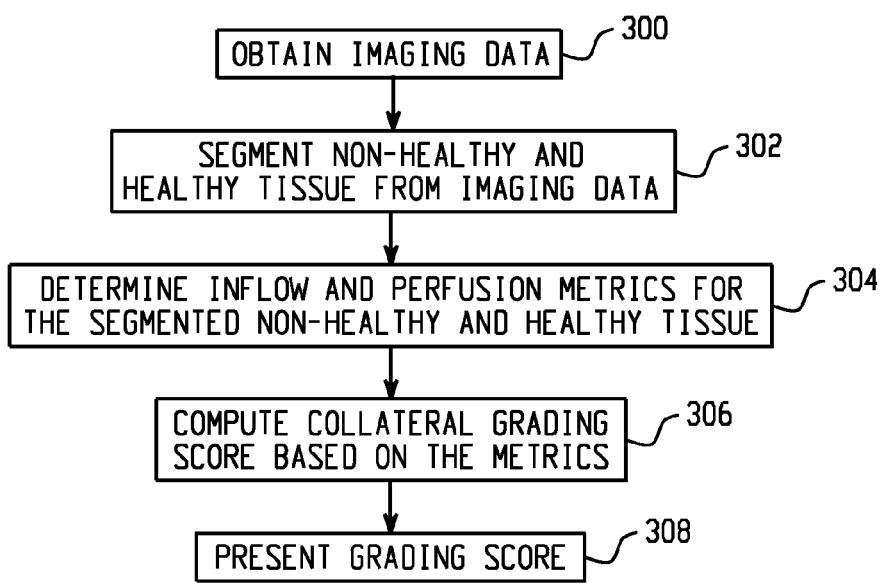
FIG. 3 illustrates an example method for assessing collateral flow based on a collateral grading score determined from both inflow and perfusion metrics for non-healthy tissue and healthy contralateral tissue.

FIGS. 2 and 3 illustrate various methods. It is to be appreciated that the acts described in the methods are for explanatory purposes and not limiting. For example, one or more of the methods may include more or less acts, including different acts. In addition, one or more acts of one or more of the methods may occur in a different order that listed. Moreover, one or more of the methods may be combined.

Initially referring to FIG. 2, a method for assessing collateral flow based on inflow and perfusion metrics for non-healthy tissue (diseased or at-risk tissue) and healthy contralateral tissue is illustrated.

At 200, various imaging is obtained as described above.

At 202, non-healthy (diseased or at-risk) tissue is segmented from the imaging data as described above.

At 204, healthy contraleral tissue is segmented from the imaging data as described above.

At 206, inflow and perfusion metrics are determined for the non-healthy tissue.

At 208, inflow and perfusion metrics are determined for the healthy contralateral tissue.

At 210, the inflow and perfusion metrics are presented respectively for the non-healthy and healthy contralateral tissue.

Optionally, at 212, the inflow and perfusion metrics are superimposed or overlaid over the imaging data and/or segmented imaging data for the non-healthy and healthy contralateral tissue.

Turning to FIG. 3, a method for generating a collateral grading score is illustrated.

Initially referring to FIG. 2, a method for assessing collateral flow based on a collateral grading score determined from both inflow and perfusion metrics for non-healthy tissue (diseased or at-risk tissue) and healthy contralateral is illustrated.

At 300, various imaging is obtained as described above.

At 302, non-healthy tissue and healthy contralateral tissue are segmented from the imaging data.

At 304, flow and perfusion metrics are determined for the non-healthy tissue and the healthy contralateral tissue based on the segmented imaging data.

At 306, a collateral grading score is computed for the non-healthy tissue based on the flow and perfusion metrics.

The collateral grading score provides an indication of the amount of the total inflow being provided by collateral flow.

At 308, the collateral grading score is presented, with or without the imaging data.

The acts described herein may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

Although the above is describe in connection with a CT scanner, it is to be appreciated that the above also applies to non-CT imaging applications in which a pre-scan image is used to plan a series of image acquisitions where patient movement may result in planned FOV no longer being a desired FOV. Examples of such imaging applications include but are not limited to MRI, interventional X-ray, and/or other imaging applications.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   acquiring, with an imaging apparatus, anatomical imaging data:
   segmenting, with a processor, imaging data corresponding to non-healthy tissue of interest and healthy tissue of interest from the anatomical imaging data
   determining, with the processor, both first inflow and first perfusion metrics for the non-healthy tissue of interest;
   determining, with the processor, both second inflow and second perfusion metrics for the healthy tissue of interest;
   computing, with the processor, a relative inflow metric based on the inflow metrics of the non-healthy and the healthy tissue of interest;
   computing, with the processor, a relative perfusion metric based on the perfusion metrics of the non-healthy and the healthy tissue of interest;
   generating, with the processor, a collateral grading score based on the relative inflow metric and the relative perfusion metric by subtracting the relative perfusion metric from the relative inflow metric to compute the collateral grading score; and
   concurrently presenting both the first inflow and perfusion metrics for the non-healthy tissue of interest and both the second inflow and perfusion metrics for the healthy tissue of interest.

2. The method of claim 1, wherein the healthy tissue of interest and the non-healthy tissue of interest have substantially similar inflow and perfusion characteristics.

3. The method of claim 1, further comprising:
   concurrently presenting the inflow and perfusion metrics respectively with corresponding imaging data for the non-healthy and the healthy tissue of interest.

4. The method of claim 3, further comprising:
   superimposing both the first inflow and first perfusion metrics and the imaging data of the non-healthy tissue of interest; and
   superimposing both the second inflow and second perfusion metrics and the imaging data of the healthy tissue of interest.

5. The method of claim 4, wherein the first and second metrics are superimposed as color maps with colors corresponding to an amount of inflow and perfusion.

6. The method of claim 1, wherein the first and second inflow respectively are arterial blood volume inflow into a first artery feeding the non-healthy tissue of interest and a second artery feeding the healthy tissue of interest.

7. The method of claim 6, wherein the relative inflow metric indicates a reduction in inflow in the non-healthy tissue relative to the healthy tissue of interest.

8. The method of claim 1, wherein a collateral grading score of zero indicates that a reduction in perfusion in the non-healthy tissue is proportional to a reduction in inflow in the non-healthy tissue, thereby indicating substantially no collateral flow.

9. The method of claim 1, wherein a collateral grading score in a range from about zero to one indicates collateral flow in the non-healthy tissue.

10. The method of claim 9, wherein a collateral grading score value within the range indicates a fraction of inflow of the non-healthy tissue that is provided by collateral pathways.

11. The method of claim 1, wherein the non-healthy tissue is diseased or at risk brain tissue and the healthy tissue is normal brain tissue.

12. A system, comprising:
   an imaging apparatus configured to acquiring anatomical imaging data; and
   a processor configured to:
      segment imaging data corresponding to non-healthy tissue of interest and healthy tissue of interest from the anatomical imaging data;
      determine both first inflow and first perfusion metrics for the non-healthy tissue of interest;
      determine both second inflow and second perfusion metrics for the healthy tissue of interest;
      compute a relative inflow metric based on the inflow metrics of the non-healthy and the healthy tissue of interest;
      compute a relative perfusion metric based on the perfusion metrics of the non-healthy and the healthy tissue of interest;
      generate a collateral grading score based on the relative inflow metric and the relative perfusion metric by subtracting the relative perfusion metric from the relative inflow metric to compute the collateral grading score; and
      concurrently present both the first inflow and perfusion metrics for the non-healthy tissue of interest and both the second inflow and perfusion metrics for the healthy tissue of interest.

13. The system of claim 12, wherein the processor concurrently presents the inflow and perfusion metrics respectively with corresponding imaging data for the non-healthy and the healthy tissue of interest.

14. The system of claim 12, wherein the processor superimposes both the first inflow and first perfusion metrics and the imaging data of the non-healthy tissue of interest and superimposes both the second inflow and second perfusion metrics and the imaging data of the healthy tissue of interest.

15. The system of claim 14, wherein the first and second metrics are superimposed as color maps with colors corresponding to an amount of inflow and perfusion.

16. The system of claim 12, wherein the first and second inflow respectively are arterial blood volume inflow into a first artery feeding the non-healthy tissue of interest and a second artery feeding the healthy tissue of interest.

17. The system of claim 12, wherein the non-healthy tissue is diseased or at risk brain tissue and the healthy tissue is normal brain tissue.

* * * * *